United States Patent
Kunin et al.

(10) Patent No.: US 9,593,382 B2
(45) Date of Patent: Mar. 14, 2017

(54) COMPOSITIONS AND METHODS FOR IDENTIFYING AND COMPARING MEMBERS OF MICROBIAL COMMUNITIES USING AMPLICON SEQUENCES

(71) Applicant: TAXON BIOSCIENCES, INC., Tiburon, CA (US)

(72) Inventors: Victor Kunin, El Cerrito, CA (US); Matt Ashby, Mill Valley, CA (US); Stewart Scherer, Orinda, CA (US); Nastassia Patin, La Jolla, CA (US)

(73) Assignee: TAXON BIOSCIENCES INC

( * ) Notice: Subject to any disclaimer, the term of this patent is extended or adjusted under 35 U.S.C. 154(b) by 548 days.

(21) Appl. No.: 14/002,627

(22) PCT Filed: Jun. 28, 2013

(86) PCT No.: PCT/US2013/048719
§ 371 (c)(1),
(2) Date: Aug. 31, 2013

(87) PCT Pub. No.: WO2014/005094
PCT Pub. Date: Jan. 3, 2014

(65) Prior Publication Data
US 2014/0162274 A1    Jun. 12, 2014

Related U.S. Application Data

(60) Provisional application No. 61/665,656, filed on Jun. 28, 2012.

(51) Int. Cl.
| | | |
|---|---|---|
| *C12Q 1/68* | (2006.01) | |
| *C12Q 1/04* | (2006.01) | |
| *G06F 19/18* | (2011.01) | |
| *G06F 19/26* | (2011.01) | |

(52) U.S. Cl.
CPC .............. *C12Q 1/689* (2013.01); *C12Q 1/04* (2013.01); *C12Q 1/6809* (2013.01); *G06F 19/18* (2013.01); *G06F 19/26* (2013.01)

(58) Field of Classification Search
None
See application file for complete search history.

(56) References Cited

U.S. PATENT DOCUMENTS

| | | | |
|---|---|---|---|
| 5,055,397 A | 10/1991 | Michaels et al. | |
| 5,093,236 A | 3/1992 | Gonzales-Prevatt et al. | |
| 5,424,195 A | 6/1995 | Volkwein | |
| 5,695,937 A | 12/1997 | Kinzler et al. | |
| 5,866,330 A | 2/1999 | Kinzler et al. | |
| 5,981,190 A | 11/1999 | Israel | |
| 6,613,520 B2 | 9/2003 | Ashby | |
| 8,071,295 B2 | 12/2011 | Ashby | |
| 8,476,016 B2 | 7/2013 | Ashby | |
| 9,206,680 B2 | 12/2015 | Ashby et al. | |
| 2001/0045279 A1 | 11/2001 | Converse et al. | |
| 2004/0033557 A1 | 2/2004 | Scott et al. | |
| 2007/0161077 A1 | 7/2007 | Pfeiffer et al. | |
| 2010/0047793 A1 | 2/2010 | Toledo et al. | |
| 2010/0093049 A1 | 4/2010 | Datta et al. | |
| 2011/0251983 A1 | 10/2011 | Ashby | |
| 2013/0030712 A1 | 1/2013 | Ashby | |

FOREIGN PATENT DOCUMENTS

WO    2012/033980 A2    3/2012

OTHER PUBLICATIONS

Barbe et al. (Microbiology, 2009, 155, p. 1758-1775).*
Ashby, Matthew N. et al., "Serial Analysis of rRNA Genes and the Unexpected Dominance of Rare Members of Microbial Communities," Applied and Environmental Microbiology, Jul. 2007, pp. 4832-4542.
Backhed, Fred et al., "Host-Bacterial Mutualism in the Human Intestine," The Inner Tube of Life, Science, vol. 307, Mar. 25, 2005, pp. 1915-1920.
Cho, et al., "The human microbiome: at the interface of health and disease", Nature Reviews, Genetics, vol. 13, Apr. 2012, 260-270.
Clarke et al., "Nutritional control of rat liver fatty acid synthase and S14 mRNA abundance," J. Nutr., 120:218-224 (1990).
Colbert et al., "Use of an Exotic Carbon Source to Selectively Increase Metabolic Activity and Growth of Pseudomonas putida in Soil," Appl. Environ Microbiol., 59:2056-2063 (1993).
Coutinho, Mario et al., "The Relationship Between Glucose and Incident Cardiovascular Events", Diabetes Care, vol. 22, No. 2, Feb. 1999, pp. 233-240.
Crump, Byron C. et al., "Microbial Biogeography along an Estuarine Salinity Gradient: Combined Influences of Bacterial Growth and Residence Time", Applied and Environmental Microbiology, vol. 70, No. 3, Mar. 2004, pp. 1494-1505.
Davis et al., "Areal Contrasts in the Abundance of Hydrocarbon Oxidizing Microbes in Soils", Appl. Microbiol., vol. 7, 1959, pp. 156-165.
Devereux et al., A phylogenetic tree of 16S rRNA sequences from sulfate-reducing bacteria in a sandy marine sediment, Appl. Environ. Microbiol., 60:3437-3439 (1994).

(Continued)

*Primary Examiner* — Stephanie K Mummert
(74) *Attorney, Agent, or Firm* — Pioneer Hi-Bred Int'l, Inc.

(57) ABSTRACT

In alternative embodiments, the invention provides computational algorithms, computer programs, software and other methods, systems and products of manufacture (e.g., computers, devices or apparatus) for identifying members of microbial communities, their abundance and distribution from amplicon sequence data, and comparing microbial communities and consortia. In alternative embodiments, the invention provides computer-implemented methods comprising a subset of, substantially all, or all of the steps as set forth in the flow chart of FIG. 1, FIG. 3 or FIG. 4. In alternative embodiments, the invention provides methods for identification of consortia, optionally followed by construction of artificial microbial consortia from pure strains or enrichment cultures. In alternative embodiments, the invention provides compositions, fluids, bioreactors, muds, reservoirs or products of manufacture comprising a synthetic microbial consortium made by the method of the invention.

16 Claims, 4 Drawing Sheets

(56) References Cited

OTHER PUBLICATIONS

Dunbar, John et al., "Empirical and Theoretical Bacterial Diversity in Four Arizona Soils," Applied and Environmental Microbiology, Jun. 2002, vol. 68, No. 6, pp. 3035-3045.
Farrelly et al., "Effect of Genome Size and rrn Gene Copy Number on PCR Amplification of 16S rRNA Genes from a Mixture of Bacterial Species," Appl. Environ. Microbiol. 61:2798-2801 (1995).
Felske et al., "Phylogeny of the main bacterial 16S rRNA sequences in drentse a grassland soils (The Netherlands)," Appl. Environ. Microbiol., 64:871-879 (1998).
Hofle, M.G., "Bacterioplankton community structure and dynamics after large-scale release of nonindigenous bacteria as revealed by low-molecular-weight-RNA analysis," Appl. Environ. Microbiol., 1992, 58(10):3387-3394.
Hood et al., "Microbial Indicators of Oil-Rich Salt Marsh Sediments," Appl. Microbiol.,vol. 30, 1975, pp. 982-987.
Hugenholtz et al., "Impact of Culture-Independent Studies on the Emerging Phylogenetic View of Bacterial Diversity," J of Bact, 180:4765-4774 (1998).
Hunt, Dana E. et al., "Evaluation of 23S rRNA PCR Primers for Use in Phylogenetic Studies of Bacterial Diversity", Applied and Environmental Microbiology, Mar. 2006, vol. 72, No. 3, pp. 2221-2225.
Janssen, Peter H., "Identifying the Dominant Soil Bacterial Taxa in Libraries of 16S rRNA and 16S rRNA Genes," Applied and Environmental Microbiology, Mar. 2006, vol. 72, No. 3, pp. 1719-1728.
Land et al., "Nonseismic methods can provide many views of a drillsite," Oil & Gas Journal, vol. 94, pp. 69-73 (1996).
Larsen et al., "The ribosomal database project," Nucleic Acids Research, 21:3021-3023 (1993).
Lee, International Search Report, PCT/US2011/040742, Feb. 23, 2012, Korean Intellectual Property Office.
Leu et al., "Identification and Phylogenetic analysis of thermophilic sulfate-reducing bacteria in oil field samples by 16S rDNA gene cloning and sequencing," Anaerobe, 4:165-174 (1998).
Liu et al., "Characterization of Microbial Diversity by Determining Terminal Restriction Fragment Length Polymorphisms of Genes Encoding 16S rRNA," Appl. Environ. Microbiol.,63:4516-4522 (1997).
Marguiles et al., "eSAGE: Managing and Analyzing Data generated with Serial Analysis of Gene Expression (SAGE)," Bioinformatics, 16:650-651 (2000).
Martiny, Jennifer B. et al., "Microbial biogeography: putting microorganisms on the map", Nature Reviews, Microbiology, vol. 4, Feb. 2006, pp. 102-112.
Matsuki et al., Distribution of bifidobacterial species in human intestinal microflora examined with 16S rRNA-gene-targeted species-specific primers, Appl Environ Microbiol., 65:4506-4512 (1999).
Muyzer et al., Profiling of Complex Microbial Populations by Denaturing Gradient Gel Electrophoresis Analysis of Polymerase Chain Reaction-Amplified Genes Coding for 16S rRNA, Appl. Environ Microbiol., 59:695-700 (1993).
Noble et al., "Natural Microbial Community Compositions Compared by a Back-Propagating Neural Network and Cluster Analysis of 5s rRNA," Appl. Env. Microbiol., vol. 63, pp. 1762-1770 (1997).
O'Malley, Maureen A., "The nineteenth century roots of 'everything is everywhere'", Nature Reviews, Microbiology, vol. 5, Aug. 2007, pp. 647-651.
Pace, "A Molecular View of Microbial Diversity and the Biosphere," Science, 276:7347-740 (1997).
Relman, "Detection and Identification of Previously Unrecognized Microbial Pathogens", Emerg Infect Dis, 4:382-389 (1998).
Sealey, Jesse, "A geomicrobiological method of prospecting for petroleum," The Oil and Gas Journal, pp. 142-146 (Apr. 1974).
Telang et al., "Characterization of the diversity of sulfate-reducing bacteria in soil and mining waste water environments by nucleic acid hybridization techniques," Can J Microbiol., 40:955-964 (1994).
Thomas et al., Sensitive and specific detection of Listeria monocytogenes in milk and ground beef with the polymerase chain reaction, Appl. Environ Microbiol, 57:2576-2580 (1991).
Torsvik et al., "High Diversity in DNA of Soil Bacteria," Appl. Environ. Microbiol., 56:782-787 (1990).
Tucker et al., "Detailed microbial surveys help improve reservoir characterization," Oil & Gas Journal, vol. 92, pp. 65-69 (1994).
Unrau et al., "Non-cloning Amplification of Specific DNA Fragments from Whole Genomic DNA digest using DNA Indexers," Gene, 145:163-169 (1994).
Velculescu et al., "Serial Analysis of Gene Expression," Science, 270:484-487 (1995).
Voordouw et al., "Characterization of 16S rRNA Genes from Oil Field Microbial Communities Indicates the Presence of a Variety of Sulfate-Reducing, Fermentative, and Sulfide-Oxidizing Bacteria," Appl. Environ Microbial, 62: 1623-1629 (1996).
Wang et al. , "Frequency of formation of chimeric molecules as a consequence of PCR coamplification of 16S rRNA genes from mixed bacteria I genomes," Appl. Environ Microbial, 63:4645-4650 (1997).
Wikstrom et al., "DNA recovery and PCR quantification of catechol 2,3-dioxygenase genes from different soil types," J Biotechnol., 52:107-120 (1996).
Wintzingerode et al., "Determination of microbial diversity in environmental samples: pitfalls of PCR-based rRNA analysis," FEMS Microbiology Reviews, 21:213-229 (1997).
Wu, Jin-Ya et al., "Effects of polymerase, template dilution and cycle number on PCR based 16 S rRNA diversity analysis using the deep sequencing method," Microbiology, 2010, 10:255, pp. 1-7.
Zhang et al., "Gene Expression Profiles in Normal and Cancer Cells," Science, 276: 1268-1272 (1997).
International Search Report mailed Oct. 31, 2013 for PCT/US2013/048719.
Written Opinion mailed Oct. 31, 2013 for PCT/US2013/048719.

* cited by examiner

COMPOSITIONS AND METHODS FOR IDENTIFYING AND COMPARING MEMBERS OF MICROBIAL COMMUNITIES USING AMPLICON SEQUENCES

CROSS-REFERENCE TO RELATED APPLICATIONS

This United States utility patent application is the §371 national phase of PCT international patent application no. PCT/US2013/048719, having an international filing date of Jun. 28, 2013, which claims benefit of priority to U.S. Provisional Patent Application Ser. No. 61/665,656, filed Jun. 28, 2012. The aforementioned applications are expressly incorporated herein by reference in their entirety and for all purposes.

FIELD OF THE INVENTION

This invention generally relates to microbial ecology, bioinformatics, computational biology and microbiology. In alternative embodiments, the invention provides computational algorithms, computer programs, software and other methods, systems and products of manufacture (e.g., computers, devices or apparatus) for identifying members of microbial communities, their abundance and distribution from amplicon sequence data, and comparing microbial communities and consortia. In alternative embodiments, the invention provides methods for identification of consortia, optionally followed by construction of artificial microbial consortia from pure strains or enrichment cultures.

BACKGROUND

One of the most important tasks in microbial ecology is identification of community members and their relative abundance. Presently, microbial communities are characterized by sequencing PCR-amplified 16S rRNA molecules and analyzing the sequences computationally. Several computational pipelines exist for such analysis, and they roughly consist of removal of low-quality reads, clustering (the task of assigning a set of objects or sequences into groups, or clusters) and classification of cluster representatives.

The clustering step is considered to be essential. This is because each sequence is considered a representative of a cell, and yet, the sequencing process is inherently erroneous, and sequences with errors may be interpreted as novel organisms. Cumulatively these errors are known to inflate estimations of community richness. Therefore clustering at 97% identity is currently the common practice in the field.

However, clustering has many inherent drawbacks. Besides sequencing mistakes, clustering absorbs genuine microbial diversity. The most common sequence in the cluster is used as a representative, while other sequences in the cluster are lost. Moreover, clusters are inherently sensitive to the input data, are not stable with time and change each time new data is added. Therefore an analysis done with N samples needs to be re-clustered and therefore re-done when N+1 sample is added. Because adding samples is a frequent operation, avoiding clustering could potentially save both researcher's and computers' time.

Analysis of community composition is only one step in interrogating a microbial community. Isolation of cultures is another valuable technique. Isolates can be sequenced to identify the sequence corresponding to the reporter (amplicon) region. However, the fluid nature of clusters means that the cluster to which the isolate is assigned may shift with regards to the number of members and distribution across samples, even for the previously analyzed datasets.

Another drawback is that the current practice of assigning taxonomic classification to representative sequences of the cluster requires re-classification after each clustering. This is a potentially computationally expensive procedure. Moreover, since representative sequences in the clusters shift, taxonomy may not be consistent, further perplexing data analysis.

Sequencing technology changes every few months. The changes mostly reduce the cost of sequence per base, or increase read length. As technology changes, new data from longer amplicons is not directly comparable with legacy data. Current solutions include either using lower-resolution old data or re-sequencing old samples. Either solution has problems: first solution discards the higher resolution that new technology can provide while the second requires extensive effort of sample collection which may not be available for older samples.

Identification of members of microbial communities is an important step towards identification of microbial consortia. Microbial consortia perform many important tasks in nature, notably biodegradation of complex compounds. These consortia are typically studied in a targeted fashion, when a task in hand is selected for interrogation, the organisms of interest are identified, and the interaction studied. This case-by-case strategy allows deep understanding of some consortia, but does not present a sweeping view of variety of consortia in nature.

SUMMARY

In alternative embodiments, this invention provides methods for the identification of microbial consortia based on the environmental distribution of microbes. The invention provides computational algorithms, computer programs, software and other methods, systems and products of manufacture (e.g., computers, devices or apparatus) for identifying members of microbial communities, their abundance and distribution from amplicon sequence data, and comparing microbial communities and consortia. In alternative embodiments, the invention uses unique truncated reads, called "tags," as representatives of organisms. Unique tags and their occurrences in samples are stored in a database.

The database may also link to other data types, such as tag classification, presence in culture collections etc. Sequencing errors are removed by: (i) trimming the reads to pre-defined region; (ii) removing low-quality truncated reads; and (iii) setting a threshold for tag minimum abundance to appear in the analysis. By avoiding clustering, the invention allows consistency of member counts when samples are added or removed. Differences in distribution of highly similar tags across samples can be used to identify ecologically distinct organisms.

In alternative embodiments, the methods use normalization for data size, and representation of microbial abundances as fraction of the total microbial count in a sample. In alternative embodiments, representation as fractions may be needed as sample sizes vary and datasets are not readily comparable without a normalization.

In alternative embodiments the abundance data is transformed by a log-transform. This transformation may be needed since there is a large natural range of the data and because abundance counts are often reproducible only to the level of order of magnitude. The log transform therefore allows one to correct for inaccuracies of the sequencing methodologies. Since log transform is not possible for 0 values, those can be substituted for arbitrary very small values.

In alternative embodiments, the invention provides computational methods for identification of community composition that use unique truncated amplicon sequences (tags) to describe composition of microbial communities. In alternative embodiments, the methods use a database to store unique tags and their distribution across sequenced samples. The databases can be relational databases, a collection of computer files or any other form of electronic data storage. In alternative embodiments, the database is maintained produced anew for a particular analysis or can be maintained for consistency across analyses and datasets.

In alternative embodiments, the database comprises unique tag sequences and their distribution across samples, and also can include any other data structures. In alternative embodiments, methods of the invention use direct mapping of tags to the database while not using clustering as an essential part of data analysis. The tags can be derived from single sequences, or from assembled or unassembled pair-end reads.

In alternative embodiments, the database may contain tags obtained with various sequencing technologies, covering different amplicon regions or different areas of the same amplicon region. Various tags identifying the same group of organisms can be linked, allowing comparison of tags obtained with various technologies of amplification, sequencing or data processing.

In alternative embodiments, the methods use a threshold of minimal occurrence of tags in a sample to reduce the number of analyzed tags and focus on more abundant tags. The threshold can refer to a minimal occurrence in one of the samples in any of the samples in the database or a combination of the methods above.

In alternative embodiments, the invention provides computer-implemented methods comprising a subset of, substantially all, or all of the steps as set forth in the flow chart of FIG. 1, FIG. 3 or FIG. 4.

In alternative embodiments, the methods comprise usage of similarity of both tag sequence and distribution across samples to identify tags that represent the same or similar groups of organisms. Thus, methods of the invention can identify distinct organisms with highly similar tags based on having a distinct distribution across samples.

In alternative embodiments, the invention provides methods for the identification of the composition or members of one or more microbial communities, or a group of microbes with correlated environmental distributions, in a sample using (a plurality of) amplicon sequences comprising:

(1) (a) providing (or given) a collection of, or plurality of, nucleic acid sequences from the one or more microbial communities, or a group of microbes with correlated environmental distributions, (herein referred to as "samples")

wherein the samples optionally comprise of one or more Bacteria, Achaea, Eukaryotes and/or Viruses, and optionally sequences are derived from a cDNA, an RNA or a DNA, and optionally sequences are derived from a nucleic acid amplification (e.g., a polymerase chain reaction (PCR) amplification) of a 16S, a 18S, a 23S or a 28S rRNA, or an rDNA (or a DNA encoding an rRNA gene), and optionally sequences are derived from a public or/and a private sequence database or databases, and optionally PCR amplification is achieved with a plurality of primer oligonucleotides, wherein each primer optionally comprises (contains, or is assigned) a "barcode" or a sample-identifying short oligonucleotide sequence, or an equivalent thereof, and optionally sequences are generated by a nucleic acid sequencer, or a high-throughput sequencer, e.g., such as a 454™ Titanium or Illumina MISEQ™ sequencer, and optionally sequences are associated with a quality score for each base, which optionally can be expressed in a FASTA-like format, or a qual, a fastq or a Standard Flowgram Format (SFF) format or an equivalent text-based format, and optionally samples are sequenced simultaneously, or on multiple instrument runs, and optionally sequence technology is consistent or varied across samples, and optionally sequences are unpaired or are pair-end, either assembled or not, and optionally representing abundances as absolute counts or fraction of total sequences obtained from a sample;

(b) processing the data described in step (a), and/or processing the data described in step (a) after modification or constriction of the database as described in step (c), as follows:

(i) optionally identifying nucleotide sequences containing sample-identifying barcodes and recording their correspondence to a particular sample, and then removing the barcodes, and discarding sequences that do not contain correct barcodes or contain barcodes that do not correspond to any samples, (ii) cutting or truncating the nucleotide sequences, or "reads", of (a), and designating the remaining region-specific nucleotide sequences as "tags" (a tag is a processed or truncated version of a read), and the remaining identified nucleotide sequences, or "reads" of step (b)(i), and keeping only predefined regions, wherein optionally the cutting or truncating can be done by recognizing conserved sequence patterns within the read (or database derived amplicon sequence) or by trimming reads at a defined length, wherein reads that are shorter than the defined length or do not match the pattern are discarded (they are not processed into a tag);

(iii) quality-filtering truncated reads by removing ambiguous truncated reads, and optionally removing low-quality truncated reads, wherein a low quality read falls below a quality threshold, wherein the quality-filtering of truncated reads optionally comprises examining quality scores for each base in the truncated read and removing all reads that that do not pass a quality threshold, wherein quality threshold is optionally defined as a requirement for each truncated read to have at least X % of bases possess a Q-score of at least Y, where X is 90% of nucleotide bases comprising the truncated read or higher and Y is Q-score of 20 or higher; and (iv) optionally taxonomically classifying the remaining tags, and optionally generating a data output comprising a description of microbial communities as counts of abundance of unique members of each community;

(v) importing the sequences and identifiers of new tags into the database described in 1(b); and (vi) importing the counts abundances of tags in samples into the database described in 1(b), and optionally log-transforming the abundances;

(c) constricting (or modifying) a database comprising the unique tags of step (b), linked to their abundances in samples;

wherein optionally the database is a Structured Query Language (SQL) database, a collection of files or any other computer-readable record, and optionally the database is consistently maintained across analyses and samples or constructed anew for each analysis, and optionally the database comprises (includes) other data structures, such as taxonomic assignment of tags, linking to isolated strains, sample metadata or equivalents thereof, and optionally the database is populated (has data) or is empty, such as before the first execution of stage (c) (step 1(c)), and optionally the abundance of tags in samples is log-transformed; and (d) exporting data of tag abundance of at least two samples from the database;

wherein a threshold is set for tags to appear in the analysis, and optionally the threshold is set by requiring a sequence to be abundant at least X % in at least Y datasets, and optionally X is 1% or less (but more than 0) and Y can be 1, or X is 0.1% or 0.2% and Y can be 2 or more, and/or the threshold is set by requiring a sequence to be abundant with absolute count of at least X in at least Y datasets, wherein optionally X is any number between 2 and 100 and Y can be 1; or, X is any number between 1 and 100 and Y can be 2 or more, and optionally representing abundances as absolute counts or fraction of total sequences obtained from a sample;

and optionally log-transforming the abundance data, and optionally data export is a table in which samples are columns, tags are rows and cells reflect abundances of the tag in the sample, thereby identifying the composition of microbial communities, or a group of microbes with correlated environmental distributions, wherein each tag is representative of a particular group of organisms, for example, a microbial strain or a taxonomic group; or (2) a process or method as set forth in FIG. 1, FIG. 3, or FIG. 4; or, a method for identifying a community composition, a microbial consortium, or a group of microbes with correlated environmental distributions, from amplicon sequences, or "reads", as set forth in FIG. 3; or, a procedure for identifying and creating synthetic consortia, or a group of microbes with correlated environmental distributions, as set forth in FIG. 4.

In alternative embodiments, the environmental distribution is a distribution from any environmental sample, such as for example, a production water, a formation water, a core samples, a drill cutting, water, a sediment or a soil; or the environmental distribution is a distribution from any environmental having a carbonaceous substrate, for example, including a natural or a man-made subsurface organic matter-rich formation, such as landfills, surface or subsurface bioreactors, or a man-made subsurface reservoir; or shale, coal, oil sands, bitumen, tar, oil, sandstone and limestone with organic debris or other hydrocarbon rich deposits or formations.

In alternative embodiments, the invention provides methods for identifying ecologically distinct strains of organisms from sequence and ecological distribution data, comprising:

(1) (a) providing (or given) a set of tag abundances in samples derived from a procedure of the invention, (b) identifying tags from (a) with high sequence similarity, wherein high sequence similarity is greater than or equal to 95% and lower than 100%, wherein optionally sequence similarity is calculated as editing distance between sequences;

(c) calculating correlation of tag distributions across samples, wherein 'correlation' can be computed by any method of measuring the distance or similarity including correlation coefficient, wherein optionally correlation is or comprises a Euclidean distance, a Pearson correlation, a vector distance, a Chi square, a city block, an ordination method that optionally comprises use of a PCA, a Bray-Curtis and/or a nonmetric multidimensional scaling (e.g., a NMS or an NMDS);

and optionally the distance measure is derived from using one tag as reference to determine expected distribution of other tags and identifying tags that have significant deviation from the expected value in one or more samples; and (d) identifying tags that have a lack of correlated distribution or high distance or low similarity values as derived from ecologically distinct organisms, wherein 'lack of correlated distribution' can be computed by any method, including when correlation coefficient (R square) is 0.06, 0.05, 0.04, 0.03 or 0.02 or lower, or when a significant deviation from the expected abundance values is observed; or (2) a process or method as set forth in FIG. 1, FIG. 3, or FIG. 4; or, a method for identifying a community composition, a microbial consortium, or a group of microbes with correlated environmental distributions, from amplicon sequences, or "reads", as set forth in FIG. 3; or, a procedure for identifying and creating synthetic consortia, or a group of microbes with correlated environmental distributions, as set forth in FIG. 4.

In alternative embodiments, the environmental distribution is a distribution from any environmental sample, such as for example, a production water, a formation water, a core samples, a drill cutting, water, a sediment or a soil; or the environmental distribution is a distribution from any environmental having a carbonaceous substrate, for example, including a natural or a man-made subsurface organic matter-rich formation, such as landfills, surface or subsurface bioreactors, or a man-made subsurface reservoir; or shale, coal, oil sands, bitumen, tar, oil, sandstone and limestone with organic debris or other hydrocarbon rich deposits or formations.

In alternative embodiments, the methods further comprises linking tags in the database described in 1(b) in which tags are produced with variety of technologies and linked within the database, wherein alternative technologies includes variation of target genes, primers, amplicon lengths, trimming region as described in (c (ii)), or other methods and technologies involved in amplicon sequencing, and the linking can optionally be in a form of a database table, file or any other computer-readable form.

In alternative embodiments, the invention provides methods for identifying a microbial consortium, or a group of microbes with correlated environmental distributions, comprising:

(1) (a) providing (given) a survey of abundances of microbes in two or more samples (which can be environmental samples), wherein abundances are optionally deduced from the number of copies of distinct gene sequences detected in each sample, and the gene is optionally a 16S rRNA gene sequence, and optionally abundances are represented as absolute counts or fraction of total;

and optionally log-transforming the abundance data;

and optionally the survey of abundances is derived from procedure of the invention;

(b) identifying distances or similarities of abundances in samples between pairs of microbes, by comparing abundances of one microbe to another microbe in each sample using distance or similarity metrics, wherein distance or similarity metrics may optionally comprise: a Euclidean distance, a Chi square, a correlation, a city block, an ordination method that optionally comprises use of a principle components analysis, a Bray-Curtis and/or a nonmetric multidimensional scaling (e.g., a NMS or a NMDS), and optionally each sample may comprise of all available samples or any fraction of samples;

(c) repeating step (b) for at least one more pair of microbes; and (d) storing the similarities obtained in step (b) and (c), optionally in a form of matrix data structure in a digital format, wherein matrix data structure is optionally stored in a computer memory, a drive, in a file, a collection of files, or a database, (e) performing either a network analysis, a cluster analysis or clustering on the similarity matrix obtained in step (d), wherein network analysis involves data representation in which microbes or tags are designated as nodes of the network and similarities between tags or microbes obtained in steps 4(b) and 4(c) are designated as edges of the network, wherein optionally cluster analysis or clustering is a hierarchical clustering, an identification of connected components, a connectivity-based clustering, a distribution-based clustering, a density-based clustering, a single-linkage clustering, a Marcov clustering (MCL) or a centroid clustering; and (f) designating microbes that are connected in the network or assigned to the same cluster as a consortium, wherein 'microbes' optionally comprise be all connected microbes in the network or all microbes in the cluster or any fraction of thereof; or (2) a process or method as set forth in FIG. 1, FIG. 3, or FIG. 4; or, a method for identifying a community composition, a microbial consortium, or a group of microbes with correlated environmental distributions, from amplicon sequences, or "reads", as set forth in FIG. 3; or, a procedure for identifying and creating synthetic consortia, or a group of microbes with correlated environmental distributions, as set forth in FIG. 4.

In alternative embodiments, the invention provides methods of making or creating a synthetic microbial consortium, or a method for making or creating a synthetic microbial consortium, or a group of microbes with correlated environmental distributions, wherein microbes are identified by a method of the invention, and further comprising the step of combining of corresponding microbial cultures, wherein microbial cultures comprise of pure strains, enriched strains or any combination of thereof.

In alternative embodiments, the invention provides methods for creating a synthetic microbial consortium, comprising:

(1) (a) providing (given) a survey of abundances of microbes in two or more samples, wherein abundances are optionally deduced from the number of copies of distinct gene sequences detected in each sample, and the gene is optionally a 16S rRNA gene sequence, and optionally abundances are represented as absolute counts or fraction of total;

and optionally log-transforming the abundance data;

and optionally the survey of abundances is derived from procedure of the invention;

(b) identifying distances or similarities of abundances in samples between pairs of microbes, by comparing abundances of one microbe to another microbe in each sample using distance or similarity metrics, wherein distance or similarity metrics may optionally comprise: a Euclidean distance, a Chi square, a correlation, a city block, an ordination method that optionally comprises use of a principle components analysis, a Bray-Curtis and/or a nonmetric multidimensional scaling (e.g., a NMS or a NMDS), and optionally each sample may comprise of all available samples or any fraction of samples;

(c) repeating step (b) for at least one more pair of microbes;

(d) storing the similarities obtained in step (b) and (c) in a form of matrix data structure in a digital format, wherein matrix data structure is optionally stored in a computer memory, a drive, in a file, a collection of files, or a database, thereby identifying the microbial consortium, or the group of microbes with correlated environmental distributions; and (e) combining of corresponding microbial cultures, wherein microbial cultures comprise of pure strains, enriched strains or any combination of thereof; or (2 a process or method as set forth in FIG. 1, FIG. 3, or FIG. 4; or, a method for identifying a community composition, a microbial consortium, or a group of microbes with correlated environmental distributions, from amplicon sequences, or "reads", as set forth in FIG. 3; or, a procedure for identifying and creating synthetic consortia, or a group of microbes with correlated environmental distributions, as set forth in FIG. 4.

In alternative embodiments, the environmental distribution is a distribution from any environmental sample, such as for example, a production water, a formation water, a core samples, a drill cutting, water, a sediment or a soil; or the environmental distribution is a distribution from any environmental having a carbonaceous substrate, for example, including a natural or a man-made subsurface organic matter-rich formation, such as landfills, surface or subsurface bioreactors, or a man-made subsurface reservoir; or shale, coal, oil sands, bitumen, tar, oil, sandstone and limestone with organic debris or other hydrocarbon rich deposits or formations.

In alternative embodiments, the invention provides computer-implemented methods comprising a process, protocol, or method, or for implementing a process, protocol, or method, of any process, protocol, or method of the invention, or a subset of any of any process, protocol, or method of the invention.

In alternative embodiments, the invention provides a computer program product for implementing any process, protocol, or method of the invention, or a subset of any of any process, protocol, or method of the invention.

In alternative embodiments, the invention provides a computer program product for processing data, the computer program product comprising: a computer-executable logic contained on a computer-readable medium configured for causing the following computer-executed step to occur: a computer-implemented method of the invention; or, a computer program product of the invention. In alternative embodiments, the computer-executable logic is further configured to cause the following steps to occur: receiving data elements or structures; and storing the data elements or structures in a memory, and optionally further comprising a step of transmitting the identified structures, or plurality or library of compounds having the desired property, and optionally the transmitting is to an interactive user capable of interacting with and/or modifying the computer program product or computer-executable logic, or the composition or members of a microbial community in a sample as identified by the method; or, a microbial consortium or a group of microbes with a correlated environmental distribution as made or identified in the method.

In alternative embodiments, the invention provides a Graphical User Interface (GUI) computer program product comprising a representation of: the compositions or members of a microbial community in a sample used or identified in any process, protocol, or method of the invention, or a subset of any of any process, protocol, or method of the invention; a plurality of compositions or members of a microbial community in a sample as made or identified in a process, protocol, or method of the invention; or, a microbial consortium, or a group of microbes with correlated environmental distributions, as made or identified in a process, protocol, or method of the invention, and optionally further comprising a step of transmitting the representations to a user.

In alternative embodiments, the invention provides a computer system comprising a processor and a data storage device, wherein said data storage device has stored thereon: (a) a computer program product for implementing a computer-implemented method of the invention; (b) a computer program product of the invention; (c) a Graphical User Interface (GUI) computer program product of the invention; or, (d) a combination thereof.

In alternative embodiments, the invention provides a non-transitory memory medium comprising program instructions for running, processing and/or implementing: (a) a computer program product for implementing a computer-implemented method of the invention; (b) a computer program product of the invention; (c) a Graphical User Interface (GUI) computer program product of the invention; or, (d) a computer system of the invention; or (e) a combination thereof In alternative embodiments, the invention provides a computer-readable storage medium comprising a set of or a plurality of computer-readable instructions that, when executed by a processor of a computing device, cause the computing device to run, process and/or implement; or, a non-transitory computer readable medium having stored therein instructions executable by a computing device to cause the computing device to perform functions comprising: (a) a computer program product for implementing a computer-implemented method of the invention; (b) a computer program product of the invention; (c) a Graphical User Interface (GUI) computer program product of the invention; (d) a computer system of the invention; (e) a non-transitory memory medium of the invention; or, (f) a combination thereof.

In alternative embodiments, the invention provides computer program storage device, embodied on a tangible computer readable medium, comprising: (a) a computer program product for implementing a computer-implemented method of the invention; (b) a computer program product of the invention; (c) a Graphical User Interface (GUI) computer program product of the invention; or, (d) a computer system of the invention; (e) a non-transitory memory medium of the invention; (f) a computer-readable storage medium of the invention; or, (g) a combination thereof.

In alternative embodiments, the invention provides a computer or equivalent electronic system, comprising: a memory; and a processor operatively coupled to the memory, the processor adapted to execute program code stored in the memory to: run, process and/or implement: (a) a computer program product for implementing a computer-implemented method of the invention; (b) a computer program product of the invention; (c) a Graphical User Interface (GUI) computer program product of the invention; or, (d) a computer system of the invention; (e) a non-transitory memory medium of the invention; (f) a computer-readable storage medium of the invention; (g) a computer program storage device of the invention; or (h) a combination thereof.

In alternative embodiments, the invention provides a system, comprising: a memory configured to: store structures or values associated with a plurality of structures or data points and/or a plurality of structures or data elements, and a processor adapted to execute program code stored in the memory to: run, process and/or implement: (a) a computer program product for implementing a computer-implemented method of the invention; (b) a computer program product of the invention; (c) a Graphical User Interface (GUI) computer program product of the invention; or, (d) a computer system of the invention; (e) a non-transitory memory medium of the invention; (f) a computer-readable storage medium of the invention; (g) a computer program storage device of the invention; (h) a computer or equivalent electronic system of the invention; or, (i) a combination thereof.

In alternative embodiments, the invention provides microbial consortium, or groups of microbes with correlated environmental distributions, made by a method, process or protocol of the invention. In alternative embodiments, the invention provides a composition, a fluid, a bioreactor, a mud, a reservoir or a product of manufacture comprising a synthetic microbial consortium made by a method, process or protocol of the invention.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of aspects of the invention and are not meant to limit the scope of the invention as encompassed by the claims.

Like reference symbols in the various drawings indicate like elements.

DETAILED DESCRIPTION

In alternative embodiments, the invention provides methods, systems and products of manufacture (e.g., computers, devices or apparatus) for identifying and comparing members of microbial communities, microbial consortia or groups of microbes with correlated environmental distributions, from amplicon sequence data, and identifying members of a microbial communication, a microbial consortium, or a group of microbes with correlated environmental distributions, from analysis of amplicon sequences. In alternative embodiments, the invention provides computational algorithms, computer programs and other methods, systems and products of manufacture (e.g., computers, devices or apparatus) for identifying members of microbial communities, their abundance and distribution from amplicon sequence data, and comparing microbial communities and consortia.

In alternative embodiments, the invention provides computational algorithms, computer programs, software and other methods, systems and products of manufacture (e.g., computers, devices or apparatus) for identifying members of a microbial community, a microbial consortium, or a group of microbes with correlated environmental distributions, their abundance and distribution from amplicon sequence data, and comparing microbial communities and consortia. In alternative embodiments, the invention uses unique truncated reads (termed tags) as representatives of organisms. Unique tags and their occurrences in samples are stored in a database. The database may also link to other data types, such as tag classification, presence in culture collections etc.

In alternative embodiments, sequencing errors are illuminated by i) trimming the reads to predefined region (see Step 2 in the Procedure) ii) removing low-quality truncated reads iii) setting a threshold for tag minimum abundance to appear in the analysis.

By avoiding clustering, this invention allows consistency of member counts when samples are added or removed. Differences in abundance distribution of highly similar tags across samples can be used to identify ecologically distinct organisms.

Figure 1:
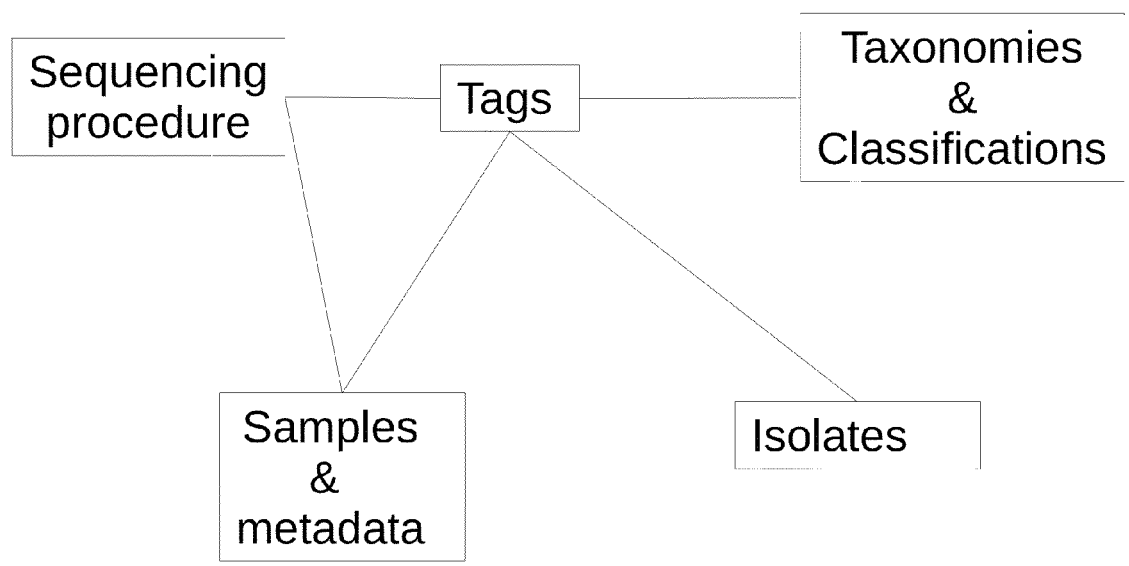
FIG. 1 schematically illustrates an exemplary schema of a database core used to practice the invention. Boxes represent major data types, lines represent connections between them. Each block represents a group of tables, spreadsheets or files. Data for tags, sequencing procedure, samples & metadata, isolates, taxonomies and classification are interlinked.

In alternative embodiments, methods, or computer implemented methods, of the invention comprise:

Database:

A database containing data from previous experiments is maintained, e.g., as illustrated in FIG. 1. The database must contain unique tags. Tags are unique nucleotide sequences trimmed to the desired region as described in step 1 of the Procedure. The database must contain records of tags occurrence across previously analyzed samples or datasets. The database may contain taxonomic classifications of tags, links to isolates or culture collections that contain tag sequences in their genomes or any other data associated with tags.

Input:

1) Sequencer output, comprising or containing reads and associated quality scores for an amplified gene (e.g., a PCR-amplified gene), which optionally comprises or is a 16S, 18S, 23S or 28S rDNA (DNA encoding ribosomal RNA).
2) A list of samples, and associated 'barcodes'. Barcodes are sample-identifying short oligonucleotide sequences included within primer sequences which allow multiplexing within a single run.

Procedure:

1) Nucleotide sequences containing barcodes mentioned in the input file are identified, and their correspondence to samples is recorded, and barcodes are removed. Sequences that do not contain correct barcodes are discarded.
2) Reads are cut to keep only predefined regions. The resulting sequences are called tags. In alternative embodiments, cutting can be done by recognizing patterns within the read or by trimming reads at desired length.

For example, length trimming to length 250 would keep bases 1 to 250 and discard other bases. Patterns can be recognized, for example, for any sequence longer than 120 base pairs (bp) recognizing the conserved patterns GGTAGTC at 5' of the sequence and AATTGNCGGGG (SEQ ID NO:1) at 3' of the sequence, allowing fewer than 2 mismatches, and resulting tag must be between 90 and 200 base pairs long. Reads that are shorter than the defined length or do not match the pattern are discarded. Multiple rules or any combination of the rules to trim sequences can be applied.

3) Low-quality truncated reads are removed. High-quality truncated reads can be identified as truncated reads in which at least X % of bases have at least Q-score of Y. Multiple rules can be implemented. For example, only keep truncated reads that have Q score of 20/25 for 100/90 percent bases, respectively, and remove truncated reads with ambiguous nucleotides (such as 'N'). Truncated reads below this threshold are considered low-quality and are removed. Other procedures for quality control can be employed, e.g., procedures as described in: Sogin (2006) Proc. Natl. Acad. Sci. U.S.A., vol. 103(32):12115-12120; P. H. Victor Kunin, "PyroTagger: A fast, accurate pipeline for analysis of rRNA amplicon pyrosequence data," The Open Journal, vol. 1, no. 1.

4) New tags (that are not present in the previous version of the database) and counts of tags in each sample are entered into the Database. The tag counts can be real counts (such as 5) or fractions of the total tags in the sample (such as 0.5% of total).

5) New tags are taxonomically classified. There are multiple alternative procedures for taxonomic classification which can be used to practice the invention, as described m e.g., in: Wu, et al. (2008) An Automated Phylogenetic Tree-Based Small Subunit rRNA Taxonomy and Alignment Pipeline (STAP). PLoS ONE 3(7):e2566.doi:10.1371/journal.pone.0002566, and references cited therein. One exemplary procedure used to practice the invention is a transfer of annotation from the closest sequence in a public database, e.g., such as a Genbank database.

6) At this stage the database contains the counts of community members reflected by tag abundances, and the taxonomy of each tag. This information needs to be presented to the human in a readable format or further computationally analyzed. Further analyses can include distribution on tags across samples; identification of microbial consortia across samples; identification of procedure biases, etc. The human-readable format may comprise a graph, a plot or a table or another form of presentation. For example, human-readable format can be a table in which samples are columns, tags are rows and cells reflect counts of the tag in the sample. A threshold is set for the sequence to appear in the analysis. For example, sequences may be required to be abundant at least X % in at least Y datasets; for example, at least 1% in at least 1 dataset. This threshold (referred as X above) can be varied by the application, with around 1% being the most useful. This procedure allows screening out rare mistakes and insignificant community members while keeping most of the important community members.

In alternative embodiments, the methods use normalization for data size, and representation of microbial abundances as fraction of the total microbial count in a sample. In alternative embodiments, representation as fractions may be needed as sample sizes vary and datasets are not readily comparable without a normalization.

In alternative embodiments the abundance data is transformed by a log-transform. This transformation may be needed since there is a large natural range of the data and because abundance counts are often reproducible only to the level of order of magnitude. The log transform therefore allows to correct for inaccuracies of the sequencing methodologies. Since log transform is not possible for 0 values, those can be substituted with arbitrary very small values, for example, at 0.01%, or below 1% abundance or an absolute count of 1.

In alternative embodiments, steps 1, 2 and 3 can be performed in any order or in parallel. In alternative embodiments, Steps 1 and 5 are not essential, for example, in one embodiment a protocol of the invention comprises Steps 2, 3, 4 and 6. Steps 4 and 5 can be done in parallel or performed in any order.

In alternative embodiments, similar procedures are used when reads are pair-end (overlapping or non-overlapping), with assembly of paired reads used whenever required, such as sequencing with an Illumina nucleic acid sequencing platform, e.g., GENOME ANALYZER IIX™ or a HISEQ SYSTEM™ (Illumina, San Diego, Calif.), or equivalent). In this procedure a read pair (assembled or otherwise) will be used as a 'read' in the procedure described above.

Output:

The output is a description of microbial communities as counts of abundance of unique members of each community. It is provided in a form of visualization (table of abundances), and stored as database or collection of files that describe unique tags, their distribution across samples as evidenced from sequencing.

Handling of Sequencing Mistakes

A distinctive feature of the invention is the representation of community members with unique tags rather than clusters. This representation allows usage of the database and does not require clustering. In alternative embodiments, the most important function of clustering is considered to be absorbing sequencing mistakes into a single representative OTU sequence that accounts for all sequences within a defined distance metric (e.g. 0.03 percent). This invention rejects the current view that without clustering the noise will obscure the signal and conclusions of community analysis will be incorrect.

This invention comprises use of the following safeguards to limit the influence of sequencing mistakes:

1) Reads are trimmed. As reads tend to accumulate more errors near the (one or both) ends, this step reduces potential errors (step 2 of the Procedure).
2) Truncated reads with high number of low-quality bases are removed from the dataset (step 3 of the Procedure).
3) Sequencing mistakes that pass the filter described in step (2) can be divided to rare and systematic. Rare mistakes in the sequencing process result in tags that have m negligible occurrence and removed by the method described in Procedure (6). Tags with errors not removed by the Procedure (6) are considered to have systematic mistakes or errors. Tags with systematic errors are expected to have correlated distribution with its 'mother', or 'correct' sequence, with the correct tag having much higher abundance and high similarity (sequence identity) to the tag with error. These traits of systematic errors allow correction in data analysis and post-processing.

Data Consistency

Prior to this Invention, each time a sample was added to a previously analyzed group of samples, analysis (including clustering and taxonomic classification) had to be re-done. Moreover, due to the nature of clustering, clusters are fluid in their nature and may add or shed unique tags. As tags are added or removed from clusters, counts of cluster abundances per sample may change. In alternative embodiments, this Invention, by usage of unique tags guarantees consistency of tag counts when samples are added or removed.

Because of the fluid nature of the clusters, prior to this Invention, linking across data types was a difficult procedure. In alternative embodiments, this Invention allows building a database with links between data types. For example, tags can be linked to taxonomic classifications, their distribution across samples, available isolates in the strain collections and other data with increased simplicity. This ability enhances operator's ability to track data.

Sequencing technology changes every few months. The changes mostly reduce the cost of sequence per base or/and increase read length. As technology changes, new data from longer amplicons is not directly comparable with legacy data. Prior to the Invention one solution was to discard advantages provided by higher resolution of newer technology and use same regions as with previous technology for consistency. Alternatively, re-sequencing of old samples was required, which mandated extensive effort of sample collection which may not be available for older samples.

In alternative embodiments, the database may contain tags obtained with various sequencing technologies, covering different amplicon regions or different areas of the same amplicon region. Various tags identifying the same group of organisms can be linked, allowing comparison of tags obtained with various technologies of amplification, sequencing or data processing. For example, if previous technology allowed sequencing of v5 region of 16S rRNA molecule and the new technology allowed sequencing of both v5 and v6 regions. Therefore tags obtained with v5-only technology may be identified as included in tags of v5 and v6 regions. If another sequence is available with v6-only region, the v5 and v6 sequences can be linked through a sequence that contains both regions. To conclude, the Invention has the ability to enable analysis of data obtained with different technology.

Identification of Ecological Divergence of Highly Similar Strains

Prior to this invention, highly similar tags (e.g., tags with high sequence similarity) were represented by a single cluster. When these tags represented ecologically different organisms, the distinction of their ecological distribution was lost and only combined distribution of all cluster members was reported. In alternative embodiments, this invention, by tracing each tag, enables comparison of ecological distributions of highly related sequences.

The invention's ability to track highly similar tags across environments provides a tool to distinguish between sequencing errors and genuinely distinct organisms. Highly similar tags may represent highly related strains or be variants within the same genome. Similar tag distributions across samples (high correlation) can be the result of variants within a genome, related strains with a similar ecological distributions or sequencing error. In contrast, highly divergent tags distributions across samples (as signified by low correlation), can only be derived from related strains with distinct ecological distribution. Therefore, in alternative embodiments, distribution of sequences across samples is used to identify ecologically relevant variants of similar organisms. The 'correlation' is any form of calculation that identifies similarity or distance and may optionally be Euclidean distance, Pearson correlation, vector distances, Chi square, city block, ordination methods that optionally comprise use of PCA, Bray-Curtis, and nonmetric multidimensional scaling (NMS or NMDS).

Tags that have high sequence similarity but do not significantly correlate can be identified as representing distinct organisms with distinct environmental distribution. However, in some cases tags representing distinct organisms may have correlated distributions. These can be identified using a slightly different procedure. One of the tags can be designated as a reference, and its distribution used to predict the distribution of a correlated tag. A significant deviation from the expected occurrence of the correlated tag in one or more samples can be used as an indication that the tag represents a distinct organism. The significance of the deviation will be established depending on the precise method chosen and there is a vast volume of literature describing evaluation of the significance of predictions depending on the methodology used.

In alternative embodiments, this invention allows utilizing additional information brought by longer tags. Prior to the invention, tags were clustered. For example, tags 100 base pairs (bp) long that had 1 difference were included in 99% clusters, as well as tags of 200 bp that had 2 differences. In alternative embodiments, this Invention uses unique tags, thereby allowing differentiating between more ecological variants as sequence length increases.

Figure 2:
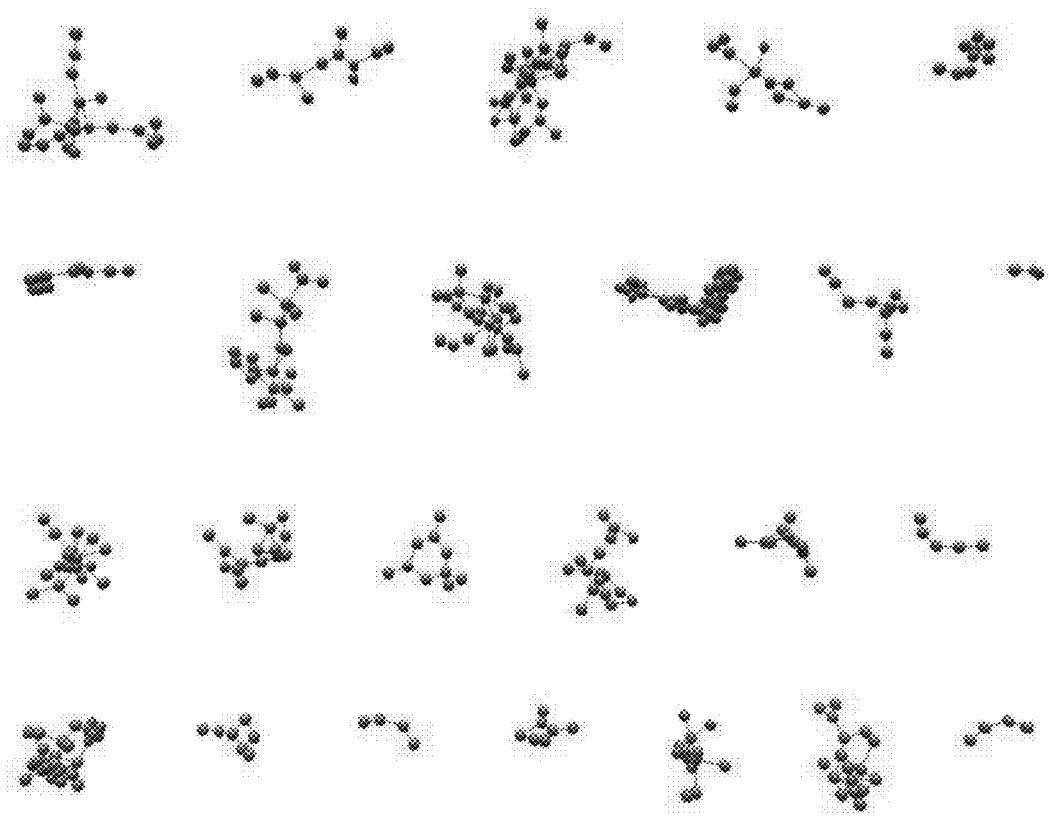
FIG. 2 illustrates a visualization of a microbial co-occurrence network, as described in detail, below.
Figure 3:
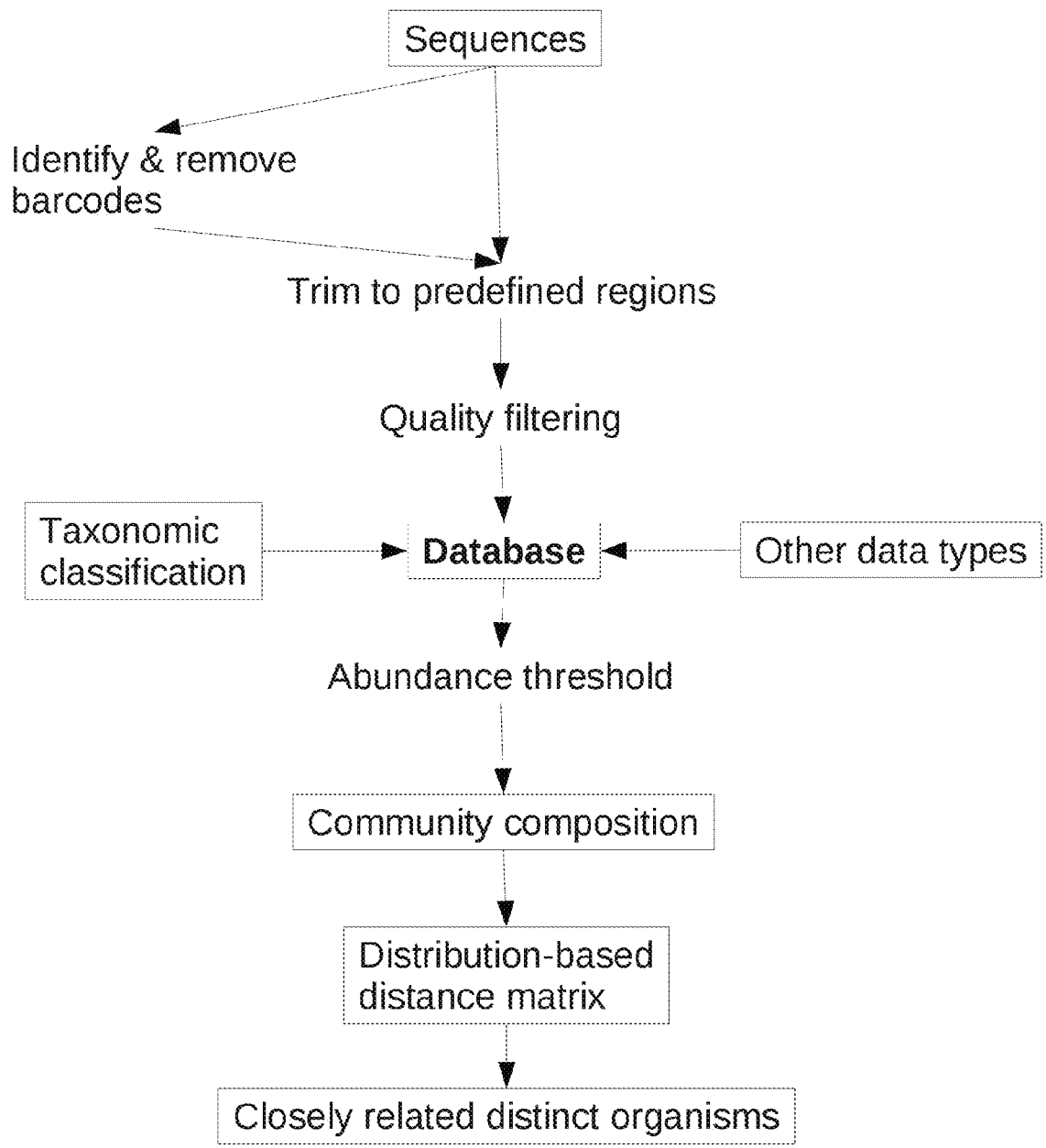
FIG. 3 illustrates an exemplary method, or procedure, of the invention, schematically illustrating a procedure of identifying a community composition from amplicon sequences, or "reads", as described in Procedures, below.
Figure 4:
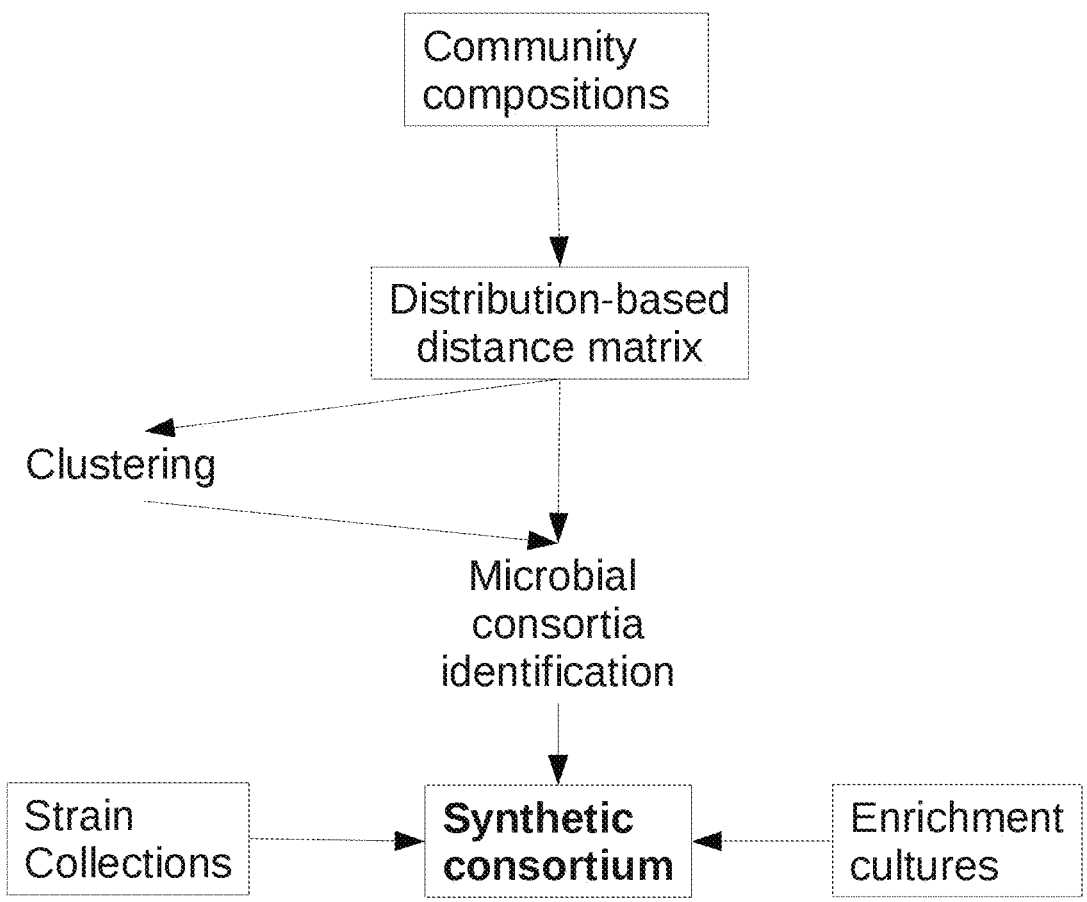
FIG. 4 illustrates an exemplary method, or procedure, of the invention, schematically illustrating a procedure of identifying and creating synthetic consortia. Community compositions of multiple samples are the input. A distance matrix for tags is computed from the distribution of tags in the samples. Groups of microbes with related distribution identified manually or by clustering, and referred to as consortia. Corresponding microbes are identified in culture collections or enrichment cultures and synthetically combined to form a synthetic consortium.

FIG. 2 illustrates a visualization of microbial co-occurrence network. This figure was derived as following: counts of microbial abundances were derived from a database that contains more than a thousand unique samples and more than 2.74 million of unique 16S rRNA tags. Only natural uncultured samples were selected for this analysis. Only tags with cumulative abundance over 100 in all samples were selected. The abundances were log-transformed. Abundances of all microbes co-occurring in more than 5 samples were compared, microbes that do not co-occur were discarded. Only counts of 10 or more were considered as presence in the sample, lower abundance was discarded. Tags that had Pearson correlation over 0.3 were considered. The correlation matrix was clustered with MCL program using inflation value 1.1. The results represented on a network in which nodes are tags and edges are correlations. Visualization is performed with a BIOLAYOUT™ program (Biotechnology and Biological Sciences Research Council (BBSRC), Swindon, UK). Due to space limitations, only a fraction of the entire network is shown. Microbial consortia are readily identified as groups of closely connected nodes on the graph.

Identification of Microbial Consortia

In alternative embodiments, the invention provides methods for the identification of microbial consortia, or groups of microbes with correlated environmental distributions. Microbial consortia perform many important tasks in nature, notably biodegradation of complex compounds. These consortia are typically studied in a targeted fashion, when a task in hand is selected for interrogation, the organisms of interest are identified, and the interaction studied. This case-by-case strategy allows deep understanding of some consortia, but does not present a sweeping view of variety of consortia in nature.

Identification of consortia is a reverse problem from identifying organisms with m similar sequences but diverse ecological distributions. In contrast, consortia often have evolutionary divergent organisms, with diverse sequences that have very similar environmental distribution. Those organisms would be interacting in nature, and those interactions can be in a form of consortia or other form of co-existence.

Microbes can have various types of interactions. For example, two microbes can be entirely mutually dependent. These microbes would also always co-occur in the same samples. A strong linear correlation of abundances of these two microbes would be expected. However, this type of interaction is reported relatively infrequently in the literature and is expected to be only a fraction of all microbial interactions. Previous analysis of sequences co-submitted to Ribosomal Database Project identified a limited group of organisms that are expected to correlate in this way.

In most cases microbes would not be absolutely dependent on each other, but would form transient interaction to participate in a consortium that performs some function. These microbes would not be always appearing together in nature. However, if they do participate in some process, for the samples where the process takes place they may be correlated. Therefore a weak(er) correlation is expected for transient consortia-formers.

Another form of correlation is anti-correlation. That is, in the same type of sample abundances of one organism is reduced when another organism is present. This interaction can be potentially observed when the organisms are mutually exclusive because of competition, or because environmental conditions that favor one organism and suppress another.

In alternative embodiments, the choice of samples for correlation analysis can be flexible. In one embodiment, an option is to choose all samples in the database. Another option is limit the samples by some characteristic. Those characteristics could be project, sample type or source, selecting only cultivation-free or cultured samples or any combination of those. Samples that are too similar to be informative can optionally be excluded.

In alternative embodiments, for identification of consortia, a data set or a database of microbial abundances in samples is required. This database can be built using a method of the invention, for example, using an rRNA, or by gene sequencing, or by any other method known in art. Abundance counts for each sequence in the database are then compared to abundance counts of other sequences in the selected choice of samples. In alternative embodiments, the sequences for which abundance counts are compared are all sequences in the database, or comprise a subsection of sequences, for example, including only abundant sequences, or only significantly different sequences, or any other subset of sequences in the database. The microbial abundances in the database may be represented as absolute counts or as fraction of the total. The abundances may further be log-transformed, for example, to better accommodate range of data and/or to correct for quantitative inaccuracies.

In alternative embodiments, the similarities of distributions of each two sequences are compared using distance metrics. These distance metrics can include either or any combination of Euclidean distance, Pearson correlation, vector distances, Chi square, city block, or ordination methods that optionally comprise use of Principal Component Analysis (PCA), Bray-Curtis ordination or Bray-Curtis dissimilarity, and nonmetric multidimensional scaling (NMS or NMDS). The most important part is that these metrics output a numerical value of distance or similarity between the two microbes or tags. An appropriate distance or similarity threshold can be used for designating similar tags, which for similarity must be greater than 0.

In alternative embodiments, the similarities between tags are stored in a matrix data structure in a computer, in form of file, database, in computer memory, or on a disk or a drive, In alternative embodiments, the similarity matrix is visualized as a network. In this network each node can be a microbe or a tag, and each edge is a similarity between them. In alternative embodiments, this network would already present consortia in a form of connected components on the graph. Areas on a graph sharing more connections are co-occurring microbes, that can be identified as consortia.

In alternative embodiments, the network may be too large and cumbersome to visualize and analyze. This is particularly true in the absence of sequence-based clustering. This form of clustering absorbs similar sequences, reducing the size of the data available for examination. In the absence of sequence-based clustering, the resolution is higher, which is matched by the increase in the size of the data. The number of components may become too large to easily examine, and the number of potential pairwise comparisons grows as a square of number of microbes (or tags) examined. Therefore, in this embodiment, reduction of the data to manageable size is desired.

In alternative embodiments, to facilitate the analysis, clustering based on environmental distribution (as opposed to sequence-based clustering) is used. Clustering is a computational technique of identifying of grouping a set of objects in such a way that objects in the same group (called cluster) are more similar (in some sense or another) to each other than to those in other groups (clusters). In this application, the objects are microbes or tags and similarity is based on environmental distribution. There are many algorithms in the art that perform clustering. In alternative embodiments, the invention comprises use of hierarchical clustering, identification of connected components, connectivity-based clustering, distribution-based clustering, density-based clustering, single-linkage clustering, Marcov clustering (MCL) and/or centroid clustering among others. In alternative embodiments, this clustering identifies groups of microbes with similar environmental distributions. Microbes that make up these clusters can be interpreted as consortia-formers.

In alternative embodiments, methods invention allow a reduction of complexity of interactions that a researcher examines from all microbes in all the tested samples down to microbes that are members of a single distribution-based cluster or a group of clusters. In alternative embodiments, the role of those microbes within a suspected consortium could be subsequently tested in a lab, where those microbes can be artificially assembled from a culture collection. This assembled community can be then assayed for performing a function of the suspected consortium, and a group of organisms required for this task identified.

Constructing Synthetic Consortia

Microorganisms rarely occur in nature as a single species. In the vast majority of cases they interact with other microorganisms that are present in the same environment, i.e., they have the same environmental distribution. Some of those interactions are of competition, while other interactions involve cooperation; or an interaction may involve competition in one aspect and cooperation in another. This invention defines organisms that tend to co-occur as a consortium and describes a procedure for identification of members of consortia and construction of synthetic consortia.

Examples of a consortium's function of interest include, for example, synthesizing or degrading a compound of interest (for example, a methanol-utilizing methanogenesis, or "methylotrophic", conversion); maintaining the health of a host organism, e.g., a human, or causing a host's disease; forming a mutually beneficial interaction with a plant, fungus or an animal; disease prevention; preservation and/or fermentation of foodstuffs (for example, as an ingredient in a probiotic), improving qualities of water or soil; biodegradation of m pollutants and pollution remediation; etc.

The bioinformatic identification of consortia above can be used to assemble a synthetic consortium. Most microbiology labs have access to strain collections in which pure strains are kept or grown in isolation from other microbes. Those strains can be identified by 16S rDNA sequencing, genome sequencing, or other methods (such as phenotypic methods, receiving strains from a trusted source, etc). Sometimes the strains cannot be purified to a desired axenic state and kept as enrichment cultures.

In alternative embodiments, the consortia identified by bioinformatics methods described in this Invention can synthetically constructed. The corresponding strains or enrichment cultures can be cross-referenced. This cross-reference can be done by 16S rDNA sequencing (when the culture has a sequence identical to the tag), or by classification to the same taxonomic group (such as species). When an exact match between a microbe identified by the bioinformatic methods described in this Invention can't be found within the culture collection, it can be substituted with a closely related organism. The closely related organism can be an organism of the same species or genus, or have 95% or more identity of tag or rRNA sequence.

The microbes identified as present in the consortium can be mixed together artificially in a laboratory, creating a synthetic consortium. The synthetic consortium can then be tested to perform the desired task of interest, such as synthetical or degrading a compound of interest.

Environmental Distributions

In alternative embodiments, the invention comprises methods for identifying and/or making microbial consortium or a group of microbes having a correlated environmental distribution, and microbial consortiums or a group of microbes made by these methods. In alternative embodiments, the environmental distribution is a distribution from any environmental sample, such as for example, a production water, a formation water, a core samples, a drill cutting, water, a sediment or a soil. In alternative embodiments, the environmental distribution is a distribution from any environmental having a carbonaceous substrate, for example, including a natural or a man-made subsurface organic matter-rich formation, such as landfills, surface or subsurface bioreactors, or a man-made subsurface reservoir; or shale, coal, oil sands, bitumen, tar, oil, sandstone and limestone with organic debris or other hydrocarbon rich deposits or formations, e.g., via the methylotrophic pathway.

REFERENCES

[1] M. L. Sogin, et al., "Microbial diversity in the deep sea and the underexplored 'rare biosphere'," Proc. Natl. Acad. Sci. U.S.A., vol. 103, no. 32, pp. 12115-12120, August 2006.
[2] C. Quince, et al., "Accurate determination of microbial diversity from 454 pyrosequencing data," Nat. Methods, vol. 6, no. 9, pp. 639-641, September 2009.
[3] P. H. Victor Kunin, "PyroTagger: A fast, accurate pipeline for analysis of rRNA amplicon pyrosequence data," The Open Journal, vol. 1, no. 1.
[4] J. Kuczynski, et al., "Using QIIME to analyze 16S rRNA gene sequences from microbial communities," Curr Protoc Bioinformatics, vol. Chapter 10, p. Unit 10.7, December 2011.
[5] V. Kunin, et al., "Wrinkles in the rare biosphere: pyrosequencing errors can lead to artificial inflation of diversity estimates," Environ. Microbiol., vol. 12, no. 1, pp. 118-123, January 2010.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from this description, it is appreciated that throughout the description, discussions utilizing terms such as "processing", "computing", "calculating", "determining", "displaying" or the like, refer to the actions and processes of a computer system, or similar electronic computing device that manipulates and transforms data represented as physical (e.g., electronic) quantities within the computer system's registers and memories into other data similarly represented as physical quantities within the computer system memories or registers or other such information storage, transmission, or display devices.

In alternative embodiments, the invention provides products of manufacture, or apparatus, for performing the operations of the invention. These products of manufacture, or apparatus, may be specially constructed for the required purposes, or they may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the method steps. The structure for a variety of these systems will appear from the description below. In addition, the present invention is not described with reference to any particular programming language. In alternative embodiments, a variety of programming languages are used to implement the embodiments of the invention as described herein.

In alternative embodiments, a machine-readable medium includes any mechanism for storing or transmitting information in a form readable by a machine (e.g., a computer). For example, a machine-readable medium includes a machine-readable storage medium (e.g., read only memory ("ROM"), random access memory ("RAM"), magnetic disk storage media, optical storage media, flash memory devices, etc.), a machine-readable transmission medium (electrical, optical, acoustical or other form of propagated signals (e.g., carrier waves, infrared signals, digital signals, etc.)), etc.

In this description, numerous details are set forth. It will be apparent, however, to one skilled in the art, that the present invention may be practiced without these specific details.

In alternative embodiments, "complementarity" can be defined as a percent identity, or a percent sequence identity e.g., in alternative embodiments, two nucleic acid strands are 80%, 81%, 82%, 83%, 84%, 85%, 86%, 87%, 88%, 89%, 90%, 91%, 92%, 93%, 94%, 95%, 96%, 97%, 98%, 99%, or more, or completely (100%) identical, or 80%, 81%, 82%, 83%, 84%, 85%, 86%, 87%, 88%, 89%, 90%, 91%, 92%, 93%, 94%, 95%, 96%, 97%, 98%, 99%, or more, or completely complementary. The more complementary two strands, the more likely the resulting code is to encode a particular protein, or in the case of the present invention, more complementary two amplicon sequences, the higher degree of certainty that two members (from which the amplicon sequences are derived) belong to the same microbial community.

Computer Systems and Data Storage Devices

In alternative embodiments, the methods of the invention, in whole or in part, necessarily require implementation using a machine, computer system or equivalent, within which a set of instructions for causing the computer or machine to perform any one or more of the protocols or methodologies of the invention may be executed. In alternative embodiments, the machine may be connected (e.g., networked) to other machines, e.g., in a Local Area Network (LAN), an intranet, an extranet, or the Internet, or any equivalents thereof. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. The term "machine" shall also be taken to include any collection of machines, computers or products of manufacture that individually or jointly execute a set (or multiple sets) of instructions to perform any one or more of the methodologies of the invention.

In alternative embodiments, an exemplary computer system of the invention comprises a processing device (processor), a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), and a data storage device, which communicate with each other via a bus.

In alternative embodiments, a processor represents one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. In alternative embodiments the processor is configured to execute the instructions (e.g., processing logic) for performing the operations and steps discussed herein.

In alternative embodiments the computer system further comprises a network interface device. The computer system also may include a video display unit (e.g., a liquid crystal display (LCD) or a cathode ray tube (CRT)), an alphanumeric input device (e.g., a keyboard), a cursor control device (e.g., a mouse), and a signal generation device (e.g., a speaker).

In alternative embodiments, the data storage device (e.g., drive unit) comprises a computer-readable storage medium on which is stored one or more sets of instructions (e.g., software) embodying any one or more of the protocols, methodologies or functions of this invention. The instructions may also reside, completely or at least partially, within the main memory and/or within the processor during execution thereof by the computer system, the main memory and the processor also constituting machine-accessible storage media. The instructions may further be transmitted or received over a network via the network interface device.

In alternative embodiments the computer-readable storage medium is used to store data structure sets that define user identifying states and user preferences that define user profiles. Data structure sets and user profiles may also be stored in other sections of computer system, such as static memory.

In alternative embodiments, while the computer-readable storage medium in an exemplary embodiment is a single medium, the term "machine-accessible storage medium" can be taken to include a single medium or multiple media (e.g., a centralized or distributed database, and/or associated caches and servers) that store the one or more sets of instructions. In alternative embodiments the term "machine-accessible storage medium" can also be taken to include any medium that is capable of storing, encoding or carrying a set of instructions for execution by the machine and that cause the machine to perform any one or more of the methodologies of the present invention. In alternative embodiments the term "machine-accessible storage medium" shall accordingly be taken to include, but not be limited to, solid-state memories, and optical and magnetic media.

In alternative embodiments, information and signals are represented using any technology and/or technique known in the art. For example, data, instructions, commands, m information, signals, bits, symbols, and chips used to practice the compositions (devices, computers) and methods of the invention can be represented by voltages, currents, electromagnetic waves, magnetic fields or particles, optical fields or particles, or any combination thereof In alternative embodiments, the various illustrative logical blocks, modules, circuits, and algorithm steps used to describe exemplary embodiments of the invention can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Modifications of this invention will occur readily to those of ordinary skill in the art in view of these teachings. The description of the invention herein is illustrative and not restrictive. This invention is to be limited only by the following claims, which include all such embodiments and modifications when viewed in conjunction with the above specification and accompanying drawings. The scope of the invention should, therefore, be determined not with reference to the above description, but instead should be determined with reference to the appended claims along with their full scope of equivalents.

What is claimed is:

1. A method for making a synthetic microbial consortium comprising:
   a) providing a plurality of nucleic acids from one or more samples;
   b) sequencing the nucleic acids;
   c) processing the sequencing reads into tags by trimming the sequencing reads at a defined length, wherein sequencing reads shorter than the defined length are discarded;
   d) quality filtering the tags by removing ambiguous truncated sequencing reads or sequencing reads that falls below a quality threshold;
   e) determining the count abundances of tags in the one or more samples;
   f) importing the sequences and identifiers of new tags into a database;
   g) importing the count abundances of tags in samples into the database;
   h) exporting data of the tag count abundance of at least two samples from the database, wherein a threshold for minimum tag abundance is set for tags to appear in a correlation analysis;
   i) creating a data output comprising description of microbial communities identified as counts of abundance of unique members of each community; and
   j) combining microbial cultures corresponding to the composition of microbes correlated with environmental distributions to create a synthetic microbial consortium.

2. A synthetic consortium made by the method of claim 1.

3. A composition, a fluid, a bioreactor, a mud, a reservoir, or a product of manufacture comprising a synthetic microbial consortium made by the method of claim 1.

4. The method of claim 1, wherein the one or more samples comprise bacteria, archaea, eukaryotes, or viruses.

5. The method of claim 1, wherein the sequencing comprises amplification of the nucleic acids, wherein the amplification uses primers comprising a barcode.

6. The method of claim 5, wherein the barcode corresponds to a sample or an environmental parameter.

7. The method of claim 1, wherein the sequencing associates each base with a quality score.

8. The method of claim 1, wherein the nucleic acids from the one or more samples are sequenced simultaneously.

9. The method of claim 1, wherein the nucleic acids from the one or more samples are sequenced on multiple instrument runs.

10. The method of claim 1, wherein the trimming of the sequences comprises recognizing conserved sequence patterns within the sequencing read.

11. The method of claim 1, wherein the tags are taxonomically classified.

12. The method of claim 1, wherein the tag abundances represent absolute counts or a fraction of total sequences obtained from a sample.

13. The method of claim 1, wherein the abundance data is log transformed.

14. The method of claim 1, wherein the data is exported in a human-readable format.

15. The method of claim 1, further comprising identifying the composition of microbes correlated with environmental factors, wherein each tag is representative of a particular group of microbes with correlated environmental distributions.

16. The method of claim 1, further comprising constricting the database.

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (7)..(7)
<223> OTHER INFORMATION: n is a, c, g, or t

<400> SEQUENCE: 1
caattgncgg gg